United States Patent [19]

Gault

[11] Patent Number: 6,149,434
[45] Date of Patent: Nov. 21, 2000

[54] METHOD FOR AUTOGENOUS TRANSPLANTATION OF HUMAN AND ANIMAL TEETH THAT ELIMINATES THE RISK OF ANKYLOSIS AND ROOT RESORPTION

[75] Inventor: Philippe Gault, Orleans, France

[73] Assignee: Societe Anonyme Natural Implant, Brest, France

[21] Appl. No.: 09/398,467

[22] Filed: Sep. 17, 1999

[51] Int. Cl.$^7$ ...................................................... A61C 5/00
[52] U.S. Cl. ................................................ 433/215; 433/1
[58] Field of Search .......................... 433/215, 1; 606/15, 606/18

[56] References Cited

U.S. PATENT DOCUMENTS

| 5,292,253 | 3/1994 | Levy | 433/215 |
| 5,455,041 | 10/1995 | Genco et al. | 433/215 X |
| 5,674,074 | 10/1997 | Angelo, Jr. | 433/215 |
| 5,695,338 | 12/1997 | Robert | 433/215 |

*Primary Examiner*—Nicholas D. Lucchesi
*Attorney, Agent, or Firm*—Young & Thompson

[57] ABSTRACT

A method for transplanting human or animal teeth while eliminating the risk of ankylosis and root resorption. This method involves stimulating the periodontal ligament prior to transplanting the teeth by causing surgical trauma to the periodontal ligament by mobilization of the teeth (extraction and immediate replantation) and retaining them in a mobilized position to cause mechanical stimulation.

24 Claims, 24 Drawing Sheets

METHOD FOR AUTOGENOUS TRANSPLANTATION OF HUMAN AND ANIMAL TEETH THAT ELIMINATES THE RISK OF ANKYLOSIS AND ROOT RESORPTION

BACKGROUND OF THE INVENTION

1. Field of the Invention

The present invention relates to a method for transplanting human or animal teeth, including mature or retained teeth, from one site to another in the mouth while eliminating the risk of ankylosis and root resorption. More specifically this method involves extracting human or animal teeth from their alveolar site of origin, reinserting said teeth into their original site and stabilizing the extracted teeth with sutures. After waiting a sufficient period of time to create a biological stimulation on the periodontal ligament due to the healing process, the extracted tooth is then transplanted in the receiving alveolus. This waiting period to achieve this biological stimulation is between about 5 and 30 days, preferably 15 days.

2. Brief Description of the Prior Art

Auto-transplantation is known in the art as a process wherein a tissue or organ is transferred by grafting the tissue or organ in the body of the same individual. In the case of dental auto-transplantation, a tooth located in one alveolus or tooth socket is transferred to a new alveolus.

Auto-transplantation of teeth has been carried out for many years by dentists, but with varying success rates. Numerous parameters and criteria have been studied and evaluated to obtain better results using various dental transplantation protocols.

It was known in the art that successful auto-transplantation of teeth can be obtained when the healing process gives a normal periodontal ligament (PDL) on the entire surface of the tooth's root, a normal epithelial attachment and collagenic "apparatus" at the gingival level. Auto-transplantation has been carried out for many years, but with varying success rates, and periodontal ligament (PDL) healing has been identified as a key success factor in order to avoid ankylosis and root resorption phenomenon. When these objectives are achieved, the auto-transplantation is generally successful in the long run. On the other hand, if the healing process generates lasting areas of inflammation and an ankylosis phenomenon, auto-transplantation prognosis will be poor or limited in time. Ankylosis causes the root of the tooth to be absorbed by the jawbone.

In order to reduce inflammation and ankylosis during auto-transplantation and thus improve the chances of success of this method, several factors were already known in the art of dentistry.

Thus, the first factor that was known in the art was that the tooth needs a live normal periodontal ligament (hereinafter referred to as PDL) around its entire surface when it is put in place into the new alveolus. This means that the root surface should not be traumatized by overpressure or contact with any surgical tools, and that it should not dry out by staying in ambient air during the transplantation surgery for too long. See, for example, Van Hassel et al., Endod Dent Traumatol.; 6:506–508 (1980); Bromlöf et al., Scand J Dent Ros., 8:441–445 (1980); Nyman et al., J. Clin Periodontal., 7:394–401 (1980); Andreasen J. O. et al., Endod Dent Traumatol. 2:76–89 (1995); Oikarinen K S, et al., J. Periodontal Res., 5:337–44 (1996); and Trope M, et al. Endod Dent Traumatol., 4:171–5 (1997).

The second factor was that the alveolus in which the tooth is transplanted must be large enough so that there is no pressurized contact between the alveolus and the tooth to be transplanted. The PDL should not be compressed and should be fed by blood. Cells from the bone tissue should not contact the roots of the teeth that would facilitate ankylosis. Furthermore it was known that PDL cells during transplant have an osseogenic potential capable of adapting to a too wide alveolus. See, for example, Oswald et al., J. Endod; 6:479–484 (1980); Trope M, et al., Endod Dent Traumatol. 4:171–5 (1997);

Moreover, it was known that the preparation of the alveolus 14 days prior to transplantation improves vascularization of the site and results as described in Nethander et al., Int J. Oral Maxillofac Surg., 17:330–336 (1988).

The third factor known in the art was that the pulpal state of immature teeth, with an open apex, could be preserved and kept alive after transplantation. However, the pulp of mature teeth, with a closed apex, often get necrosed after transplantation. Necrotic or infected pulpal tissue is the cause of inflammatory processes that in turn will provoke root resorption.

Moreover, it was known that endodontic treatment can be performed within 10 to 20 days after transplantation to avoid inflammatory resorption. Filling is done preferably with $Ca(OH)_2$ at this stage. Andreasen J. O. Swed Dent J.,; 4:135–144 (1980); Andreasen J. O., Swed Dent J., 7:245–52 (1981) and Swed Dent J., 8:135–144 (1982); Trorstad et al., J. Endod., 8:17–22 (1981).

Furthermore, it was also known that splinting of the transplanted tooth should never be rigid, but should allow limited movements of the tooth and thus a functional stimulation. If a rigid splint is needed it should be restricted to 4 weeks. Andreasen J. O., Acta Odontol Scand., 33:313–323 (1975); Andreasen J. O. Int J. Oral Surg., 12:239–249 (1983); Berude J. A. et al., J. Endod., 14:592–600 (1988); Oikarinen K. Endod Dent Traumatol. 6:237–50 (1990); Gupta S, et al. J Clin Pediatr Dent. 22(1):19–21 (1997); and Mandel U, et al. Arch Oral Biol. 34(3):209–17 (1989).

It was also known that systemic antibiotic therapy significantly reduces root resorption. Hammarström L.et al., Endod Dent Traumatol., 2:51–59 (1986) and Sae-Lim V, et al. Endod Dent Traumatol., 14(5):232–6 (1998).

Thus, in the prior art the protocol for auto-transplanting a tooth involved the procedural steps of antibiotherapy treatment, local anesthesia of the tooth, extraction of the tooth to be replaced, preparation of the alveolus (curettage, enlargement), extraction of the dental transplant without tool impact on the root surface, placing the transplanted tooth into the alveolus at a level identical to the previous tooth and using a suture splint for immature teeth, while for mature teeth a wire stabilized by a composite was utilized.

After the auto-transplantation was performed, post surgical X-rays were generally taken.

Several follow up cessions at various time intervals were then performed. For example after 8 days the sutures were removed; at 21 days the splint was generally removed and the root canal was then filled with $Ca(OH)_2$ if the tooth was mature. After 28 days X-rays were again taken and a check up of root resorption risk was usually performed. After 8 weeks X-ray control was performed. After 6 months the transplanted tooth or teeth were checked to determine whether the $Ca(OH)_2$ filling was in order or final filling was completed. This latter procedure is again performed after 1 year.

Thus, it can be concluded from the above that auto-transplantation of a tooth or teeth by the prior art methods was a long and tedious procedure requiring frequent monitoring of the patient after transplantation.

Unfortunately, the outcome of the procedures taught in the prior art was not that successful and it has been shown that after 5 years on mature teeth, healing with normal PDL and without ankylosis-root resorption occurred in only 12% of transplanted Molars, in 62% of transplanted Premolars and in 48% of transplanted Incisors. See, Andreasen J. O. Atlas de réimplantation et de transplantation dentaires, Editors Masson, (1992); Andreasen J O, et al., *Eur J Orthod.*, 12(1):3–13 (1990); and Andreasen J O, et al., *Eur J Orthod.* 12(1):25–37 (1990).

Therefore, a need still remains in the dental art to provide a method for transplantation of teeth that will reduce or eliminate ankylosis and root resorption and therefore result in a higher tooth transplantation success rate.

Thus it is an object of the present invention to improve the success of auto-transplantation for teeth in animals or humans.

It is a further object of the present invention to provide a process for eliminating the risk of ankylosis and root resorption after auto-transplantation of teeth.

It is a further object of the present invention to create a biological stimulation of the periodontal ligament, thus aiding in reducing the risks of ankylosis and root resorption.

It is yet a further object of the present invention to provide various suturing techniques that will aid in reducing the risks of ankylosis and root resorption.

In yet another further aspect of the present invention is to provide a method for stimulating desmodonts.

In yet a further aspect of the present invention is to provide a method for regenerating the tooth alveolus ligament, particularly on a retained tooth.

In another aspect, the present invention further provides a method for regenerating bone around a human or animal tooth and more particularly an alveolus bone or a collateral bone in any osseus site.

In yet another aspect, the present invention provides a method for stimulating bone formation.

These and other objects are achieved by the present invention as evidenced by the summary of the invention, description of the preferred embodiments and the claims.

SUMMARY OF THE PRESENT INVENTION

The present invention provides a method for auto-transplanting a human or an animal tooth said method comprising the steps of:
  (a) extracting said human or animal tooth to be transplanted from the alveolus of origin;
  (b) suturing immediately said extracted human or animal tooth back into said alveolus of origin;
  (c) waiting for a period of time to facilitate stimulation of the periodontal ligament of said human or animal tooth to be transplanted; and
  (d) transplanting said extracted tooth having a stimulated periodontal ligament in a new receiving alveolus.

In another aspect of the present invention provides a method for stimulating a desmodont of a human or an animal tooth said method comprising the steps of:
  (a) extracting said human or animal tooth from the alveolus of origin;
  (b) suturing immediately said extracted human or animal tooth back into said alveolus of origin; and
  (c) waiting for a period of time such that a very large quantity of biologically stimulated PDL fibroblasts are generated in the tooth alveolus ligament.

In yet another method aspect the present invention provides a method for regenerating bone, said method comprising the steps of:
  (a) extracting said human or animal tooth to be transplanted from the alveolus of origin;
  (b) suturing immediately said extracted human or animal tooth back into said alveolus of origin;
  (c) waiting for a period of time to obtain stimulated periodontal ligament cells in said extracted human or animal tooth; and
  (d) placing said extracted tooth in a new alveolus for a period of time to regenerate said bone in any osseous site.

In yet another method aspect, the present invention provides a method for suturing extracted teeth such that splinting of the transplanted tooth is avoided.

DETAILED DESCRIPTION OF THE PREFERRED EMBODIMENTS OF THE PRESENT INVENTION

Figure 1A:
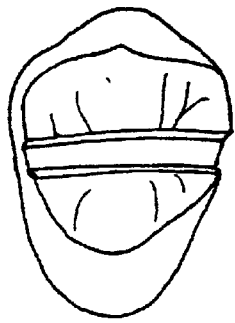
FIG. 1 are drawings of a tooth illustrating the particular suturing procedures used in the method of the present invention.
Figure 1B:
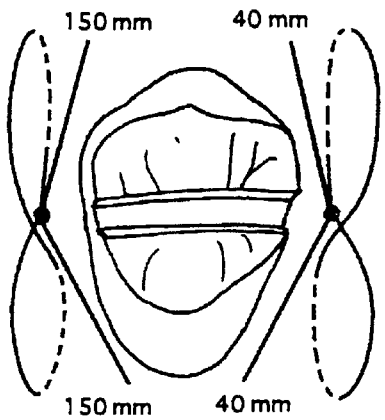
Figure 1C:
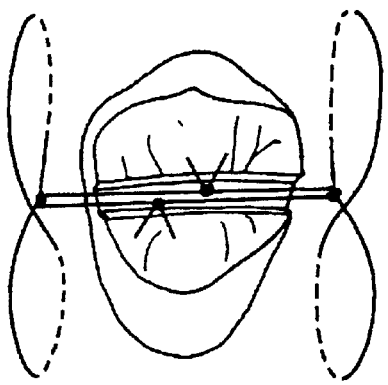
Figure 1D:
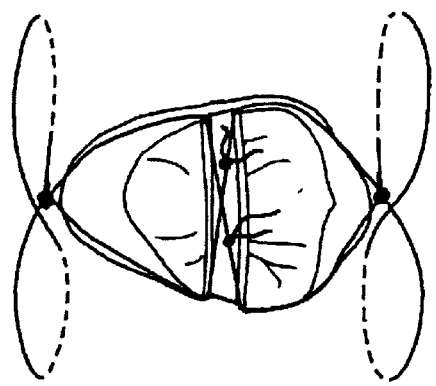
Figure 1E:
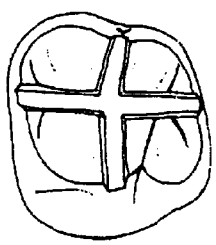
Figure 1F:
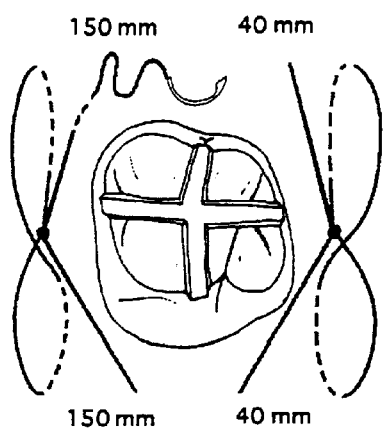
Figure 2A:
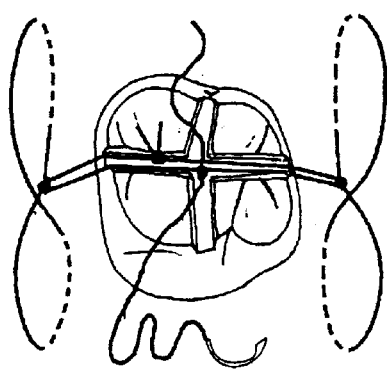
FIG. 2 are additional drawings of a tooth illustrating the particular suturing procedures used in the method of the present invention.
Figure 2B:
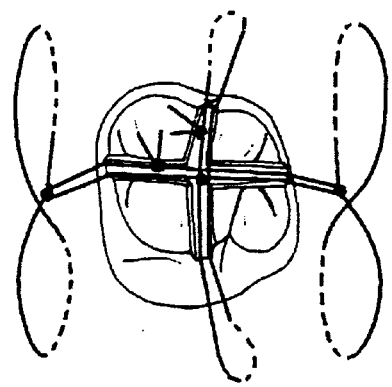
Figure 2C:
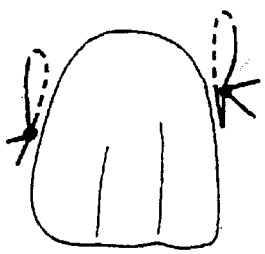
Figure 2D:
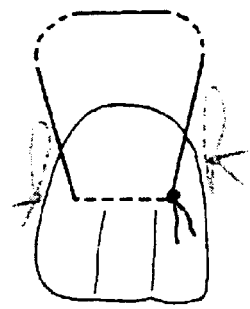
Figure 2E:
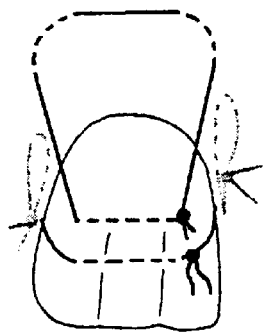
Figure 2F:
Figure 3A:
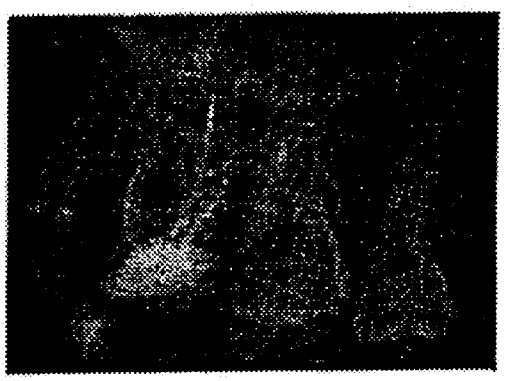
FIG. 3 are photographs of teeth illustrating the method of the present invention displaying the presurgical X-ray, preliminary treatment and the beginning of the extraction-replantation; i.e., mobilization of the tooth to be transplanted. A picture illustrating the suture technique utilized in this part of the procedure is also shown.
Figure 3B:
Figure 3C:
Figure 3D:
Figure 3E:
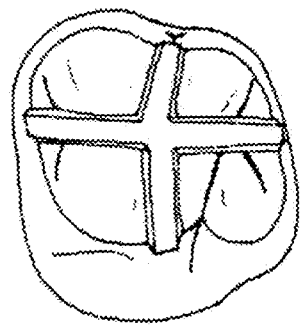
Figure 3F:
Figure 4A:
FIG. 4. are photographs of teeth illustrating the method of the present invention displaying part of the extraction-replantation; i.e., mobilization of the tooth to be transplanted.
Figure 4B:
Figure 4C:
Figure 4D:
Figure 4E:
Figure 4F:
Figure 5A:
FIG. 5 are photographs of teeth illustrating the method of the present invention displaying the completion of the extraction and mobilization of the tooth to be transplanted. Also shown in this Figure is the beginning of the tooth transplantation process.
Figure 5B:
Figure 5C:
Figure 5D:
Figure 5E:
Figure 5F:
Figure 6A:
FIG. 6 are photographs of teeth illustrating the method of the present invention displaying part of the tooth transplantation process.
Figure 6B:
Figure 6C:
Figure 6D:
Figure 6E:
Figure 6F:
Figure 7A:
FIG. 7 are photographs of teeth illustrating the method of the present invention displaying the completion of the tooth transplantation process. Pictures illustrating the suture technique utilized in this part of the procedure are also shown.
Figure 7B:
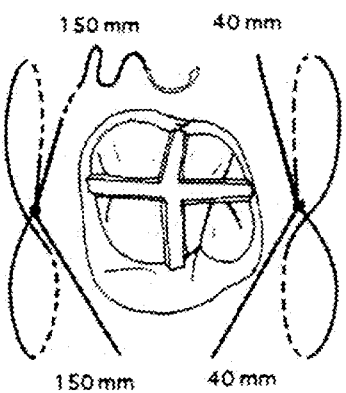
Figure 7C:
Figure 7D:
Figure 7E:
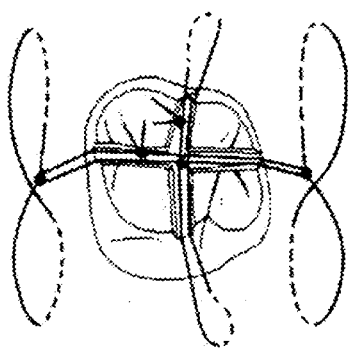
Figure 7F:
Figure 8A:
FIG. 8 are photographs of the various sutures used in the method of the present invention, as well as photographs of the status of the transplanted tooth thirty days after transplantation.
Figure 8B:
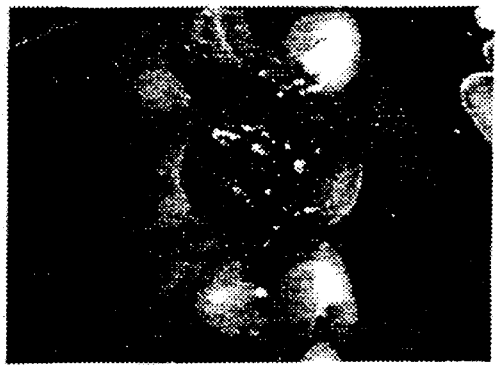
Figure 8C:
Figure 8D:
Figure 8E:
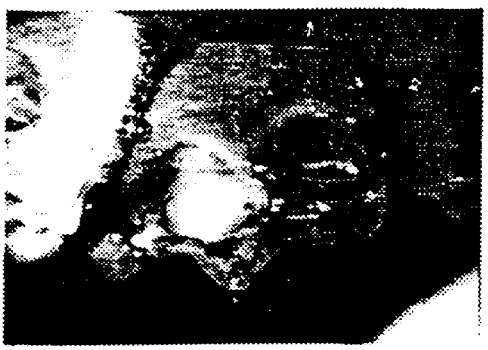
Figure 8F:
Figure 9A:
FIG. 9 are follow-up photographs and X-rays of teeth after completing the method of the present invention. Radiography showed a complete adaptation of the bone alveolus to the root having a normal periodontal ligament width.
Figure 9B:
Figure 9C:
Figure 9D:
Figure 9E:
Figure 9F:
Figure 10A:
FIG. 10 are photographs of teeth showing a specific embodiment using the method of the present invention wherein the patient had undergone a traumatic extraction of one tooth and further orthodontia treatment was needed and undertaken on the transplanted tooth.
Figure 10B:
Figure 10C:
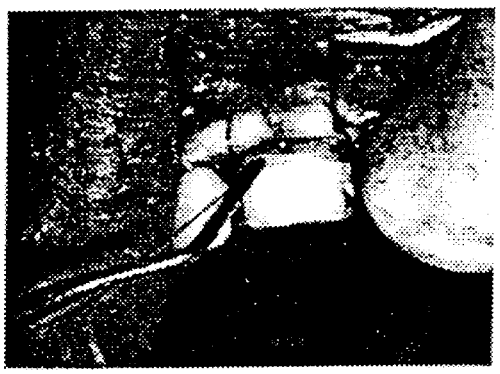
Figure 10D:
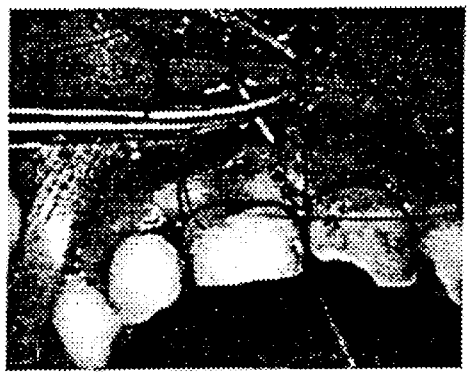
Figure 10E:
Figure 10F:
Figure 11A:
FIG. 11 are photographs and X-rays of teeth illustrating the orthodontia treatment after transplantation using the method of the present invention shown in FIG. 10.
Figure 11B:
Figure 11C:
Figure 11D:
Figure 11E:
Figure 11F:
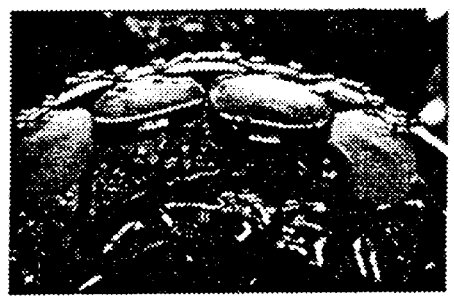
Figure 12A:
FIG. 12 are photographs and X-rays of teeth showing another specific embodiment using the method of the present invention wherein the patient had lost a tooth due to root fracture and the replacement tooth was non-functional.
Figure 12B:
Figure 12C:
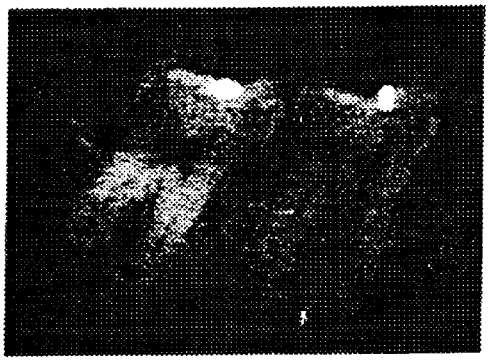
Figure 12D:
Figure 12E:
Figure 12F:
Figure 13A:
FIG. 13 are photographs of teeth after transplantation using the method shown in FIG. 12 in which coronal restitution was additionally performed.
Figure 13B:
Figure 13C:
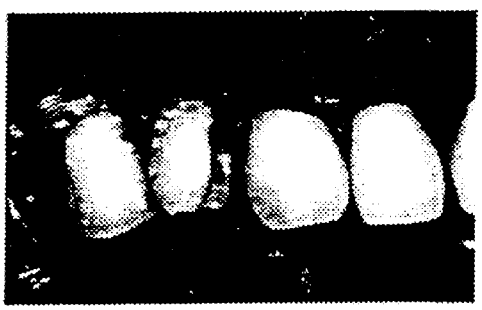
Figure 13D:
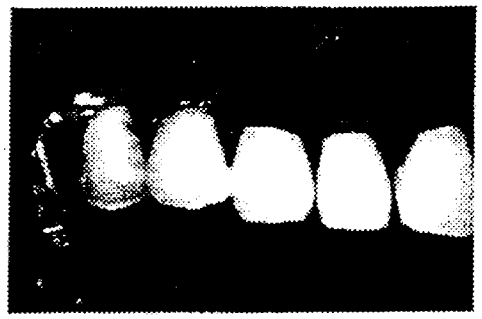
Figure 13E:
Figure 13F:
Figure 14A:
FIG. 14 are follow-up photographs and X-rays of teeth showing the results of the present invention using the method shown in FIGS. 12 and 13.
Figure 14B:
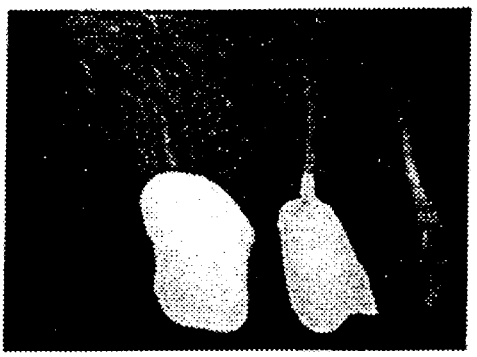
Figure 14C:
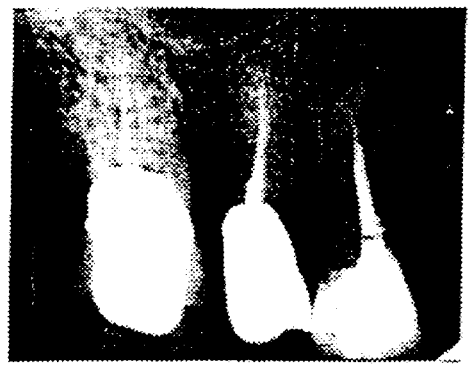
Figure 14D:
Figure 14E:
Figure 15A:
FIG. 15 are photographs and X-rays of teeth showing another specific embodiment using the method of the present invention in which the tooth transplanted by the method of the present invention was later used as one of five abutments to anchor a bridge.
Figure 15B:
Figure 15C:
Figure 15D:
Figure 15E:
Figure 15F:
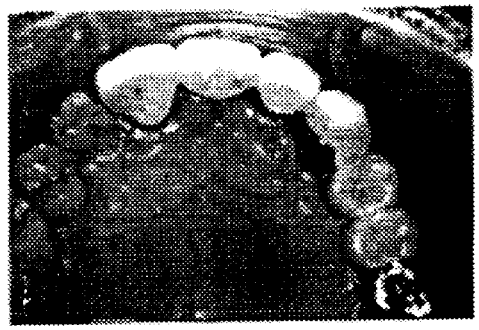
Figure 16A:
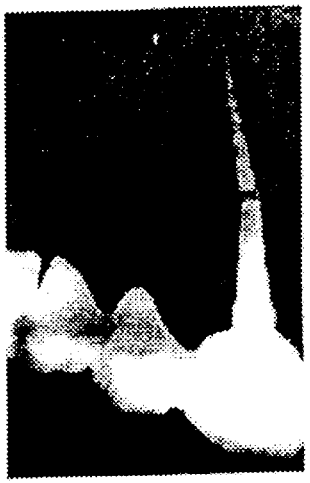
FIG. 16 are follow-up X-rays of teeth after the bridge was anchored on the transplanted tooth using the method shown in FIG. 15.
Figure 16B:
Figure 16C:
Figure 16D:
Figure 16E:
Figure 16F:
Figure 17A:
FIG. 17 are photographs and X-rays of teeth showing another specific embodiment using the method of the present invention in which the alveolus was modified and two molar half's of a tooth were transplanted.
Figure 17B:
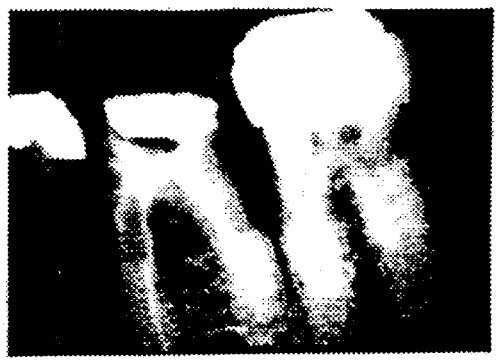
Figure 17C:
Figure 17D:
Figure 17E:
Figure 17F:
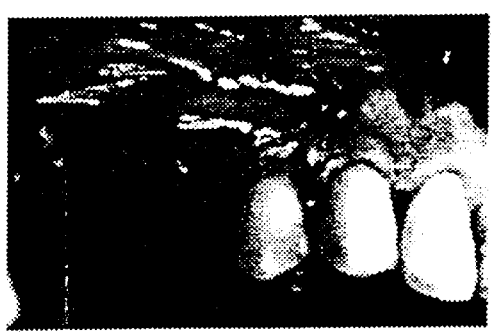
Figure 18A:
FIG. 18 are photographs and X-rays of teeth illustrating the suturing procedure, coronal restoration and follow-up radiographs after the transplantation of two molar half's of a tooth using the method shown in FIG. 17.
Figure 18B:
Figure 18C:
Figure 18D:
Figure 18E:
Figure 18F:

As used herein the word "tooth" used in the singular also encompasses more than one tooth and encompasses natural mature teeth, retained teeth, part of one or more tooth (one root) and artificial teeth, including non osseo-integrated dental implants with or without a temporary crown. Any type of tooth can be used in the method of the present invention including molars, incisors, premolars and canines.

Examples of the types of artificial teeth that can be used in the method of the present invention include, but are not limited to, those described in WO 97/45533, EP 0 734 712, Patent Abstracts of Japan, vol. 14 no. 086 (C-690 (1990) and JP 01 299563 by Moritsuga, Ootori et al (1989), as well as those described in Hanes et al, *Journal of Periodontology*, vol. 60, no. 4 pgs. 188–198 (1989).

As used herein the term "a large quantity of fibroblasts" means the proliferative induction of PDL cells when a healing repair occurs after breaking in the middle of the periodontal ligament by mobilization (extraction and immediate replantation) of a tooth. Thus upon healing repair three to ten times the normal amount of fibroblasts are regenerated.

As used herein the term "mechanical stimulation on the periodontal ligament" means that occlusal pressure under physiologic conditions (i.e., mastication, swallowing and the like) induce limited and episodic movements of the teeth in the alveolus. These movements are limited by the tightening of the PDL fibers and the sutures. The alveolus can be ectopic.

As used herein the words "desmodont" and "ligament" used in the singular also encompass the plural forms of these words. It being appreciated by the skilled artisan that a single tooth has a sole ligament and desmodont and the method of the present invention is not limited to utilizing the method on only one tooth; i.e., several teeth can be autotransplanted at the same time.

Indeed, the present invention was based on the discovery that reducing ankylosis and root resorption after transplantation of a tooth, can be achieved when the tooth of interest is transplanted with a stimulated periodontal ligament. This is accomplished by creating a trauma to the PDL of the tooth to be transplanted prior to transplantation and maintaining the tooth under a certain amount of non-rigidity, which creates a mechanical stimulation of the periodontal ligament.

By "creating a trauma to the PDL" is meant that the tooth is mobilized to disrupt the PDL via extraction-immediate replantation. It is the sole method to provoke trauma and the healing process on the entire surface of the PDL. If the tooth is an artificial tooth (implant) the stimulated PDL is obtained by an organotypic culture. One example of an organotypic culture is described, for instance, in WO97/45533.

When the extracted tooth is mobilized there is generally a waiting period prior to transplantation of the tooth to permit the stimulation of the desmodonts that will contain a very large quantity of activated fibroblasts that regenerate the tooth-alveolus ligament. This delay permits the tooth to recuperate and regenerate from about 10% to 20% of the fibers in the ligament and thus the tooth is subjected to a reduced trauma during the second surgical step. Moreover, by subjecting the tooth to this waiting period the root of the tooth is covered with new conjunctive tissue which is in a high growth stage at the time of transfer transplantation (Mandel and Viidik 1989).

Generally this waiting period should be of sufficient time to permit the stimulation of a large quantity of fibroblasts and is between about 5 to 30 days, preferably about 15 days.

The fibroblasts generated in this manner can also be aspirated and used in cell culture, tests or grafts if so desired. It will be appreciated that in this instance, the tooth is not further transplanted.

After the waiting period the tooth is then transplanted using known dentosurgical techniques.

More specifically, this method entails five phases, which are the preparation of the tooth to be transplanted and the preparation of the receiving alveolus, a transplantation phase, a post surgical check, a temporary crown restoration and the completion of a final crown.

Prior to beginning this procedure a patient is generally subjected to a general check up that includes an evaluation of the patient's general status, the buccal status of the patient and the type of tooth which needs to be replaced, which can be either a missing tooth or a tooth that cannot be preserved any longer. Once this evaluation has taken place, the mouth of the patient is searched to see whether there is a non-functional tooth or a root of a non-functional tooth that can be adapted to the tooth that will be replaced. The tooth that will be transplanted can also be a retained tooth or an artificial tooth. In some cases a functional tooth can be used depending on the therapeutic strategy for a better buccal rehabilitation.

If there is access to the tooth to be transplanted the endodontic treatment is done beforehand, for example, a week before. The tooth is filled with a final filling or alternatively with a $Ca(OH)_2$ filling. This last option has no influence on the protocol outcome. If the tooth is retained, endodontic treatment will be started approximately 3 weeks after transplantation and finalized when the tooth has achieved sufficient stability.

Before the mobilization of the tooth or root, preliminary scaling and root planning are performed to avoid contamination by bacterial plaque or calculi. The mouth is rinsed with Chlorhexidine gluconate at 0.2%, twice a day, over a 4 to 8, preferably 5 week period.

After the scaling and root planning, which procedures should be undertaken by not touching the root surface with the vital PDL under epithelial attachment, an occlusal mesio-distal groove for stabilizing the sutures and a coronoplasty on the transplanted tooth is performed (FIG. 1 (1)). The tooth must be at a minimum of 1 mm under occlusal contact if any occlusal contact in fact exists. If only one root is used hemisection is performed before mobilization.

On a molar, a second bucco-lingual groove is performed (FIG. 1(5)).

The tooth to be transplanted or the dental section to be transplanted is then extracted. A supra-crestal incision is made with a surgical blade No. 12 to free up gingival attachment. For the extraction, only a forceps adapted to the crown can be used to avoid damaging the root surface. Under no circumstances should syndesmotomes and elevators be used which damage cement and desmodontal fibers. Forceps should be used to break the alveolus-tooth ligament by small progressive rotations and rocking movements.

Once the extraction is completed the root is rapidly measured in length and at its maximal and minimal diameters are taken with a periodontal probe. The total length is also measured. The root must be kept moistened by blood to maintain the vitality of ligament cells and the cementoblasts present at the root surface. The tooth is then put back in the alveolar site as quickly as possible; i.e., immediately. A suture thread going through the groove (see below) will maintain the tooth to the gum (FIG. 1 (3)).

If the tooth to be replaced is still in place, it is extracted and the alveolus is carefully curetted. The alveolus is then modified with a bone drill and bur to match the volume of the root to be transplanted. The alveolus must be larger than the root to be transplanted. The "play" must be at least one-millimeter. The root should never be forced on the alveolus wall when it is put in place. It is useful to control the alveolus size by placing the transplant into the alveolus for testing and checking. When the bone crest is too thin, a bone flap can be mobilized for enlargement of the receiving alveolus. In a situation where a cyst or a previous periodontal lesion or injury has resulted in the alveolus being much larger than the root, this procedure will not be effected. The transplanted tooth or root is then placed back into its original alveolus, is stitched with a suture fixed in the gum and going through the occlusal groove.

If the tooth to be replaced is absent, the alveolus must be entirely created with graduated implantology drills and shaped with a bone bur once the muco-periosteal flap has been elevated. The volume of the alveolus is controlled as discussed above and the flap is then stitched up.

If the root of the transplant will emerge in a maxilla sinus, the alveolus is drilled down to the Schneiderian membrane then the flap is closed back.

The transplantation surgery is performed from about 3 to 30 days, preferably about 15 days after the mobilization of the transplant and the adaptation or the creation of the receiving alveolus.

The benefit of this time delay is to transplant the tooth with a stimulated desmodont that will contain a very large quantity of fibroblasts that are regenerating the tooth-alveolus ligament. By not performing the transplantation at the time of the first surgical trauma of the ligament is the most important point of this method because in the first days after the extraction-reimplantation the desmodont is entirely destroyed and replaced by granulation tissue before it starts to self-regenerate. The delay enables the extraction of the tooth for a second time with reduced trauma because 10 to 20% of the fibers will have regenerated and the root is covered with a new conjunctive tissue which is in a high growth stage (Mandel and Viidik, 1989).

Specific ligament tissue stimulation will be improved if the transplant is put back in its original alveolus as opposed to being put directly into its final site, because the healing process occurs in the middle of the ligament and not between two different tissues; i.e., the ligament and the bone.

This stimulated tissue will regenerate the alveolus bone around the tooth in its transplanted site, whatever the bone status of this site.

Retained teeth are accessed by opening up a flap and an osteotomy at the crown level is performed. They are then extracted without touching the root, measurements of the roots are taken and they are put back in place and the flap is closed. Pulpectomy is done about 3 weeks after transplantation.

The bone alveolus is also prepared 15 days beforehand. During the transplantation surgery it is necessary to make sure that the alveolus does not contain any epithelial tissue or any necrotic tissue and that the gingival edge can be joined to the cervical surface of the transplanted tooth.

To remove retained palate canines it may be necessary to expose part of the root. A lot of care is needed to avoid damaging the cement. It is possible to cut part of the crown to ease the extrication.

The alveolus should be made such that the major axis of root section is in the direction of the mesio-distal line. This is often required when a tooth or a molar root is to be placed on a narrow bone crest. For example, an upper premolar to be transplanted on a distal wedge.

Another typical situation is that in the absence of 2nd premolar and molars in the upper distal unilateral wedge, it makes sense to position the distal root of the lower 2nd molar in the place of the 2nd premolar, with the major axis of the root section in the bucco-lingual direction, and the mesial root in the place of the first molar, with the major axis of the root section in the mesio-distal direction.

It is important during the mobilization phase to record the final orientation of the roots in their destined alveolus when they will be transplanted (notes in patient file). For example, the distal face of the distal root of the 2nd lower molar in the mesial face of 2nd upper premolar.

Whether a modified or non-modified alveolus is used in the transplant process, consequent to the extraction done 15 days before hand, the stitches joining the gingival edges are removed. Generally the gingival opening has been narrowed during the 15 days of healing, thus facilitating the adaptation between the tooth and the gum. A superficial zone of the alveolus is curetted to remove epithelial tissue migrating inside the alveolar. A deeper zone is curetted to eliminate healing tissue in the center, while the inner walls are curetted softly.

When the alveolus is re-created on a crest, the stitches are removed, the flaps are opened with a periosteal elevator and the alveolus is curetted softly.

When the alveolus opens up in the maxillary sinus, the stitches are removed, the flaps are opened with a periosteal elevator and the alveolus is curetted softly. In this case, the healing process of the alveolus after 15 days creates a thickening of the sinus mucosal membrane and a plug of healing tissue in the bottom of the bone alveolus is generally found. This plug is gently pushed back in the sinus and the sinus mucous membrane is pulled away over 5 to 10 mm around the alveolus with the use of special sinus membrane elevators. The transplant must be able to push back the mucosal membrane without creating any tension on the membrane. It is essential that the mucous does not get punctured to avoid any risk of contamination. The space between the mucous membrane and bone cortical will be colonized by healing bone tissue.

The transplant which as been mobilized 15 days before hand, is handled with forceps, without touching its roots, and extracted carefully. A small proportion of connective fibers is reformed and the tooth is extracted easily and with minor trauma.

The tooth is immediately put in the prepared alveolus, keeping the orientation as planned previously, to best adapt its emerging profile to the root profile, and the root surface covered with a desmodont to the available gingival profile.

When the flap has to be adapted to the tooth cemento-enamel junction, the flap edge is held with a rongeur and the flap is adapted to the tooth contour with a surgical blade No. 12. The junction between the flap edge and the tooth must be as sealed as soon as possible. The tooth can be put back in its original location for a short time when the flap is cut.

Prior to suturing the transplanted tooth, it must be ensured that the transplant is at least 1 mm below the occlusal contact. If there is contact, the occlusal groove can be deepened to make sure that the stitches will stay below the occlusion.

Since the healing process pushes the tooth out of the alveolus and since the transplant must be free of any contact during the first 2 to 4 weeks after transplantation, the 1 mm gap prevents the transplant from making excessive occlusal contact.

The transplant is always held in place by sutures and never with a splint connected to other teeth. This gives the tooth some mobility, which will favor ligament growth and inhibit bone tissue development.

A rigid splint transmits strain to other teeth, blocks the functional stimulation of fibroblasts and favors the growth of the bone tissue resulting in tooth ankylosis. Thus, the use of a rigid splint should be avoided.

Rivalry between the ligament and bone tissue during the healing process must be managed during all of the transplantation protocol because factors generating an ankylosis appear within less then one hour after the tooth has been transplanted and not months or years later.

A first suture brings together the gingival papilla or flap edges on the distal side of the tooth. Both sutures are cut at a distance of approximately 40 to 50 mm from the suture knot (FIG. 1(2)).

A second simple suture has the same role on the mesial side of the tooth. Suture threads should be left approximately 15 cm long for future use (FIG. 1(2)).

One of the mesial suture threads is knotted with one of the distal threads going across the occlusal groove. The same is done for the remaining suture threads (FIG. 1(3)). In some cases the groove is not mesio-distal oriented but rather bucco-lingual. For example, when an upper premolar is moved to a narrow crest at the lower molar level, the tooth is then positioned with a rotation of 90°. Suture threads are set out in a configuration forming a figure "8", going around the cuspids and in the groove (FIG. 1(4)).

For molars, two grooves, one mesio-distal and one bucco-lingual, are made (FIG. 1(5)). On the mesial suture, the needle is retained for the next step (FIG. 1(6)) after the occlusal knot is made in the mesio-distal groove with a thread of the distal suture (FIG. 2(1)). The needle passes through the lingual (or palatal) gum, and then by the buccal gum and a stitch in the occlusal groove is made with the second thread of the last knot (FIG. 2(2)).

For anterior teeth, additional stitches are used to bring together the papilla and to close up the flap (FIG. 2(3). To retain the tooth, a suture thread is bonded in the middle of the buccal face of the tooth crown with a composite, then stitched in the buccal gum twice, mesially and distally, and finally knotted (FIG. 2(4)).

A second thread is bonded on the buccal face (FIG. 2(5)), but goes along the palate side where it is stitched in the fibromucosal twice using mattress suture (FIG. 2(6)). The tooth is thus stabilized in bucco-lingual orientation.

Occlusion is checked one more time and teeth are altered if necessary to allow a space of approximately 1 mm under occlusal contact. Because the sutures stay inside the occlusion groove, or on the buccal side of anterior teeth, there are no obstacles to occlusion adjustments.

Suturing can be done on the area where the tooth has been removed. When the tooth is located at a sinus level, a circular thread on the cemento-enamel junction going above the other thread stitches, prevents the tooth from sinking.

Antibiotic therapy starts one day before the mobilization of the tooth, and is administered during a period of four weeks to prevent bacterial proliferation in surgical areas. For example, methacycline (300 mg Lysocline®) can be administered twice a day for 2 days, followed by once a day for 28 days along with analgesics such as Diantalvic (dextropropoxyphene and acetominophen (Tylenol®)). Besides antibiotics the mouth can be rinsed with Chlorhexidine at 0.2% for 1 minute twice a day for 45 days. Piasclédine (a mixture of avocado and soybean) can also be given once a day for 30 days in unfavorable cases as in the case where the alveolus is very wide or if the sinus is involved.

Post surgical controls are then performed 7 days after transplantation. These controls include an occlusion check, a suture stability check, a flap sealing check and supra-gingival cleaning with an ultrasound scaler and an antiseptic such as $H_2O_2$ at about 0.02% volume. No curette nor air-polisher is used at this point in the procedure.

Fourteen days after the transplantation, all of the stitches are removed and a supra-gingival cleaning with an ultrasound scaler and an antiseptic such as $H_2O_2$ at approximately 0.02% volume is performed.

Healing of the transplanted tooth is very fast when the alveolus has been prepared with the proper shape. The crown can be remolded with a composite to obtain an adequate morphology, in particular with occlusion points, a cosmetic buccal side and proximal contact points. Occlusal contact points during excursive movements have to be totally avoided. No heavy pressure should be applied to the tooth at this stage. A dam can be installed if the clamp is fixed on a more distal tooth.

If the alveolus was too wide or if the tooth is located on a sinus, it can be rebuilt 4 to 8 weeks after transplantation. If many teeth or roots are transplanted at the same time to a site with a major bone deficit, it is possible to join them together in order to increase their stability. This is accomplished always with a bonded composite (FIG. 24(3)).

Three to six months after the transplant, the transplanted tooth can be crowned or be used as a bridge pillar. It is preferable to wait a little longer with a composite temporary crown.

In order to further illustrate the present invention and advantages thereof, the following specific examples are given, it being understood that the same are intended only as illustrative and in nowise limitative.

EXAMPLE 1

Preoperation Radiography and Preliminary Treatment

Patient 1 was subjected to a general checkup and X-rays were taken of the teeth in the mouth. From the X-rays it was determined that the first molar in Patient 1 had a deep carious lesion and a half root length furcation lesion and thus had to be replaced. The third molar, which is nonfunctional and in healthy condition was chosen for transplantation (FIG. 3(1)). Preliminary treatment was started and scaling and root planning was completed, particularly on the tooth to be transplanted (FIG. 3(2)).

The transplanted tooth needed additional endodontic treatment and this was performed by filling the 3rd molar with $Ca(OH)_2$. The patient was then treated with antibiotics, analgesics and was requested to rinse the mouth twice a day with 0.2% Chlorohexydine for the next five weeks.

Mobilization of the Transplant (extraction and immediate replantation)

After the Preliminary treatment, Patient 1 returned for mobilization of the tooth to be transplanted. In this session the cuspids were reduced to avoid occlusal lateral stress after the transplantation (FIG. 3(3)).

A mesio-distal occlusal groove was then created on the third molar of the tooth to be transplanted. A second bucco-lingual groove was also made (FIG. 3(4)). When the groove was made it was at least 2 mm under occlusal contact after the transplantation so that the sutures will not cut if occlusal adjustments were needed (FIG. 3(5)).

Supra-crestal incision with a surgical blade no. 12 was then made around the donor tooth to be replaced to cut supracrestal gingival fibers (FIG. 3(6)). The same incision separates the safe tissue from the pathologic tissue (granulation tissue of the periodontal lesion) around the tooth to be replaced (FIG. 4(1)).

The roots of the first molar which was diseased were separated with a surgical bur and saline irrigation was performed throughout this procedure (FIG. 4(2)). The roots of the first molar were extracted carefully to preserve the osseous wall of the receiving alveolus (FIG. 4(3)).

The receiving alveolus was carefully curetted to suppress all granulation tissue (FIG. 4(4)). Since the third molar had only one root, the receiving alveolus was modified with a surgical bur under saline irrigation to suppress interradicular septa (FIG. 4(5)).

The third molar was then extracted with forceps (when possible the forceps were modified with small latex cushions to avoid fracture of the tooth). Once the crown was surrounded by the forceps, the tooth was excised by using small, progressive rotary and rocking movements (FIG. 4(6)).

The transplant tooth was then placed in the receiving alveolus. Only the PDL surface was under the gingiva. If the alveolus is too small, it can be modified again with the bur (FIG. 5(1)).

The tooth to be transplanted was then placed in the alveolar site of origin and to retain the tooth, a mesio-distal suture was placed in the groove of the tooth (FIG. 5(2)). Sutures were then placed that drew the gingival edges nearer around the receiving alveolus during the first healing period (FIG. 5(3).

A waiting period of fifteen days occurred prior to transplantation.

Transplantation of the Tooth

After the 15 day waiting period, the sutures on the third molar of Patient 1 were removed (FIG. 5(4)). The surface of the teeth and mucosa were then cleaned using an ultrasonic tip and antiseptic irrigation using a 0.02% solution of hydrogen peroxide (FIG. 5(5)).

A mesio-distal incision was then made on the receiving alveolus (FIG. 5(6)). After 15 days of healing the proliferative edge of the gingiva should be joined to the cemento-enamel junction of the transplanted tooth, even if it is smaller than the previously extracted tooth.

After the incision muco-periosteal reflection on a few millimeters with a periosteal elevator on the buccal and palatal sides was then performed (FIG. 6(1)) and curettage of the alveolar site was done to eliminate any epithelial or necrotic tissues from the receiving alveolus (FIG. 6(2)).

The tooth to be transplanted was then re-extracted from the alveolar of origin with minimal trauma (FIG. 6(3)). The forceps did not touch the vital ligament on the root transplant when re-extracted (FIG. 6(4)).

The transplanted tooth was then immediately placed in the receiving alveolar site that was previously prepared keeping the orientation as previously planned (FIG. 6(5)). The flap edge was adapted to the transplanted tooth contour with a new incision being made.

Suturing the Transplanted Tooth in the Receiving Alveolar

An inter-papillary distal suture was then made (FIG. 6(6)).

A mesial suture that brought together the gingival papilla on the mesial side of the tooth was then performed (FIG. 7(1)). Both suture stitches were cut at a minimal length of 40 mm on the distal side and at a length of approximately 120 mm on the mesial side (FIG. 7(2)). One of the mesial suture threads was then knotted with one of the distal threads going across the occlusal groove (FIG. 7(3)). A second knot was then made with the other threads (FIG. 7(4)). A bucco lingual suture was then realized from the central occlusal knot (FIG. 7(5)). The donor alveolus was then closed by suturing (FIG. 7(6)).

FIG. 8(1) illustrates a buccal view of the sutures on Patient 1. FIG. 8(2) illustrates an additional palatal suture which stabilized the transplant in excellent alignment with the other teeth. An occlusal adjustment was made to avoid any occlusal contact on the transplant (FIG. 8(3)).

Follow up on Transplanted Tooth

Patient 1 returned to have a follow up 15 days after the tooth was transplanted. At this time the sutures were removed and the area surrounding the transplanted tooth was cleaned ultrasonically and checked for occlusal control (FIG. 8(4)). The buccal view of the transplanted tooth was at 30 days (FIG. 8(5)) illustrated very good healing of the gingival (FIG. 8(5)). An X-ray was then taken and the space between the root and alveolus was noted (FIG. 8(6)).

One month after transplantation, a new cleaning with an ultrasonic scaler and hydrogen peroxide (0.02%) was made (FIG. 9(1)). The teeth appeared colored by chlorhexidine digluconate. A mobility test was further done (FIG. 9(2)).

Two months after transplantation, the gingiva appeared normal (FIG. 9(3)) without any sign of inflammation. Radiography showed osseous healing around the root (FIG. 9(4)).

Definitive endodontic filling and composite coronal restoration were performed.

Four months after transplantation, probing of the gingival sulcus showed normal depth as shown in FIG. 9(5). Radiography showed a complete adaptation of the bone alveolus to the root with a normal periodontal ligament width (FIG. 9(6)).

EXAMPLE 2

Patient 2 (15 years old) had undergone a traumatic extraction of his tooth #8 (FIG. 10(1)). Reimplantation could not be performed since the incisive was not found within the required time to preserve the vital PDL.

An orthodontic treatment was planned with one upper premolar extraction on each side. Tooth #13 was chosen for replacement of tooth #8 (FIG. 10(2)).

The steps of the transplantation protocol were the same as in Example 1; i.e., endodontic treatment with a Ca(OH)$_2$ filling; the mobilization of tooth #13; the adaptation of the alveolus in site of tooth #8; a 15 day healing period; and the coronal reduction of tooth #13 to match the coronal volume of the central incisor.

FIG. 10(3) shows the transplanted tooth #13 in which the interpapillary stitch pressed the gingival edge which provides the best contact with the cemento-enamel junction.

A suture thread was bonded horizontally on the buccal side of the crown with a composite resin. This suture was anchored by two steps of mattress stitch in the buccal gum (FIG. 10(4)) and knotted. A second thread was bonded on the buccal side (FIG. 10(5)) and was anchored on the palatal mucosa in the same manner (FIG. 10(6)).

After 14 days, the healing was very good (FIG. 11(1)) and the sutures were removed.

A radiographic comparison (FIG. 11(2)) showed alveolus adaptation, inter-radicular bone regeneration and the absence of root resorption during the first 12 months.

9 months after the transplantation, orthodontic treatment began (FIG. 11(3)). A palatal view (FIG. 11(4)) showed the interdental spaces at this time. 13 months after transplantation (FIG. 11(5)) dental movements can be clearly seen. On the palatal side, (FIG. 11(6)), interdental spaces were reduced and the transplanted tooth was coming in contact with the palatal stay of the orthodontic system. This movement proved the absence of ankylosis.

FIG. 11(5) illustrates that the buccal gum outline found its past proximal design. A further correction should be performed before definitive coronal restoration.

EXAMPLE 3

Patient 3 was a 67 year old female who had lost her tooth #5 after a root fracture. Thus, tooth #31 was non-functional (FIG. 12(1)). The extraction of tooth #5 was performed 6 months ago. The alveolus was completely healed as shown in FIG. 12(2). Radiography of tooth #31 (FIG. 12(3)), showed the right root and a furcation near the cemento-enamel junction. This morphology was favorable to transplant the distal root of tooth #31.

The protocol followed during the transplantation was generally the same as the protocol used in Example 1.

Endodontic treatment, hemisection and mobilization of the distal root of tooth #31 were performed as shown in FIG. 12(4).

14 days later, the half distal part of tooth #31 was re-extracted (FIG. 12(5)). Part of the stimulated periodontal ligament was present on the entire root surface. The forceps did not touch the root surface, to preserve vital PDL and cement from traumatic injuries. This half molar was placed in a new alveolus in the tooth #5 site as shown in FIG. 12(6). A little flap was made to adapt the gingiva in the best manner. Only the suture technique retained the tooth as shown in FIG. 13(1).

14 days after transplantation, the healing was very good and permitted coronal reconstitution immediately (FIG. 13(2)). A dental dam was placed with a clamp on tooth #4 (FIG. 13(3)) and a composite coronal reconstitution was performed as shown in FIG. 13(4) and FIG. 13(5). The mesial part of tooth #31 was left in place.

One month post-op (FIG. 14(1)), gingival healing was good and the transplanted tooth was functional. FIG. 14(2) shows a radiography performed just after the transplantation. FIG. 14(3) shows a radiography 24 months later. No ankylose-resorption was distinguishable. FIGS. 14(4) and 14(5) showed the tooth 24 months after transplantation.

EXAMPLE 4

Patient 4 is a 49 year old male. Tooth #6 had a vertical root fracture with deep bone resorption due to infection and abscesses (FIG. 15(1)+(2)). This tooth had to be replaced.

The protocol followed during the transplantation was generally the same as the protocol used in Example 1.

FIG. 15(3) shows a radiography of tooth #11 retained in the palate. This tooth was chosen for replacement of tooth #6. It was mobilized and left 14 days in its site in the left palate. At the same time, tooth #6 was extracted and its alveolus was carefully curetted.

After this period, tooth #11 was re-extracted and put in place of tooth #6 and retained only by sutures (FIG. 15(4)).

Two years later, a large bridge was performed where the transplanted tooth was one of five abutments (FIG. 15(5)+(6)). The transplanted tooth was used for a temporary bridge abutment only after six months of healing to reduce the risk of ankylosis. The presence of bruxism is also a factor to reduce risk of ankylosis.

FIG. 16 shows the radiographic follow up:

FIG. 16(1): tooth #6 before extraction

FIG. 16(2): t=+6 months

FIG. 16(3): t=+12 months

FIG. 16(4): t=+24 months

FIG. 16(5): t=+3.5 years

FIG. 16(6): t=+4.5 years

No signs of ankylosis-root resorption was noted.

EXAMPLE 5

Patient 5 was a 60 year old female. She had lost all of her upper left molars. The residual mesial root of tooth #14 had a deep periodontal lesion and had to be extracted (FIG. 17(1)).

The protocol followed during the transplantation was generally the same as the protocol used in Example 1.

Tooth #18 was used for transplantation (FIG. 17(2)+(3)). Endodontic treatment, hemisection and mobilization of each tooth was performed as shown in FIG. 17(4). During the same appointment, the alveolus was created in the upper maxilla with bone burs. The form of the osseous crest was used to its best advantage during this procedure.

The distal root of tooth #18, with the smallest diameter, was chosen to be transplanted in the mesial alveolus with its larger diameter in bucco-lingual direction.

Distally, the crest was narrower, and the distal alveolus was created with the largest axis in a mesio-distal direction for the mesial root of tooth #18. The size of each alveolus was controlled by placing its respective transplanted each half-tooth #18 until any forced contact would be suppressed between the root and the bone for the tooth's best position as illustrated in FIG. 17(5). Final orientation of the roots in their destined alveolus was recorded in the patient's file for the next appointment. The upper flap was then sutured as illustrated in FIG. 17(6).

After a delay of 15 days, the two half molars were transplanted in the upper alveolus. Sutures were made similar to those illustrated in FIGS. 1(3) and 1(4). On the distal half tooth, the sutures were set out in a configuration forming a FIG. 8 as illustrated in FIG. 18(1+2).

Fourteen days after the transplantation, all of the stitches were removed and a supra gingival cleaning with an ultrasonic scaler and an antiseptic ($H_2O_2$ at 0.02%) was performed as illustrated in FIG. 18(3).

Coronal reconstitution was made with a composite resin placed jointly between the two parts as shown in FIG. 18(4). At this time occlusal contact was avoided. After 45 days, the new composite bonding had normal occlusal contacts.

Figure 19:
FIG. 19 is an X-ray showing normal PDL space after the transplantation of two molar half's of a tooth using the method of the present invention shown in FIG. 17.
Figure 20A:
FIG. 20 are photographs and X-rays of teeth showing yet another specific embodiment using the method of the present invention in which the tooth transplanted by the method had complete alveolar bone resorption following furcal invasion and follow-up radiographs.
Figure 20B:
Figure 20C:
Figure 20D:
Figure 20E:
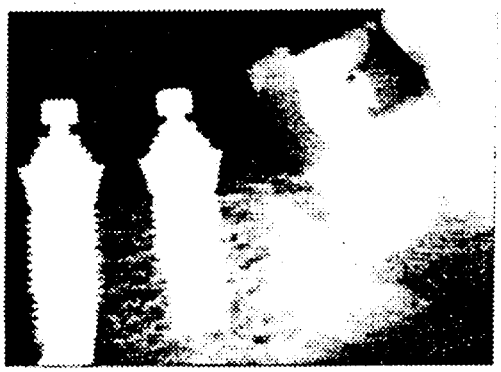
Figure 20F:
Figure 21A:
FIG. 21 are photographs and X-rays of teeth demonstrating the healing capacity of the stimulated PDL in a very old patient using the method as shown in FIG. 20.
Figure 21B:
Figure 21C:
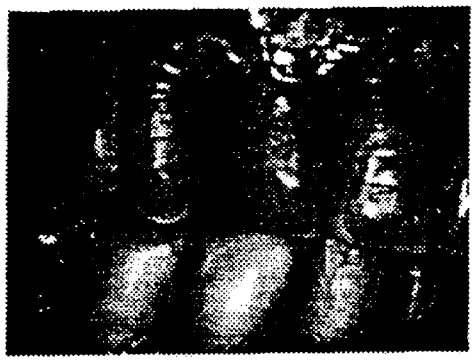
Figure 21D:
Figure 21E:
Figure 21F:
Figure 22A:
FIG. 22 are photographs and X-rays of teeth showing another specific embodiment using the method of the present invention in which the residual bone between the lesion and sinus was completely destroyed and two parts of the tooth is being transplanted. The suturing procedure for this type of procedure is also illustrated.
Figure 22B:
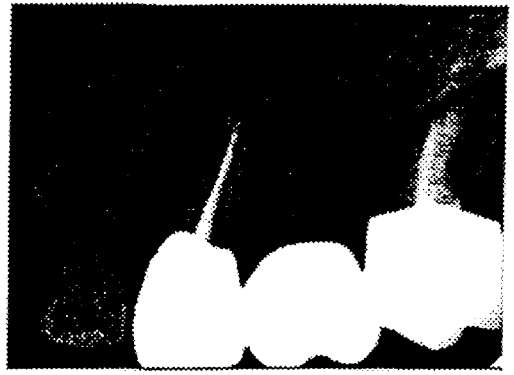
Figure 22C:
Figure 22D:
Figure 22E:
Figure 22F:
Figure 23A:
FIG. 23 are photographs of teeth illustrating another embodiment using the method of the present invention on teeth in which two parts of a tooth are transplanted and coronal restoration is performed.
Figure 23B:
Figure 23C:
Figure 23D:
Figure 23E:
Figure 23F:
Figure 24A:
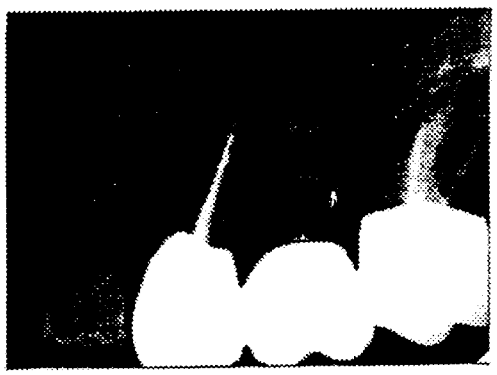
FIG. 24 are follow-up X-rays of teeth illustrating that the method of the present invention shown in FIGS. 22 and 23 has the capacity to stimulate PDL and regenerate completely destroyed bone.
Figure 24B:
Figure 24C:
Figure 24D:
Figure 24E:
Figure 24F:
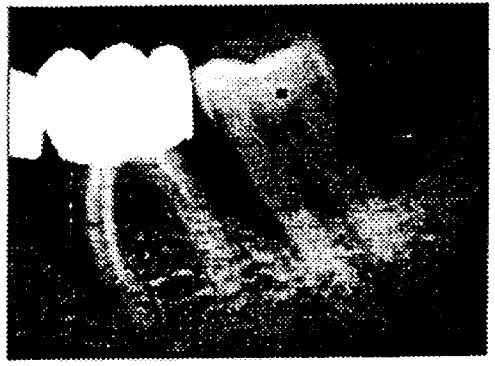

FIG. 18(5) shows a radiography of the transplanted tooth at day 15. FIG. 18(6) shows the buccal view at day 120. FIG. 19(1) shows the radiography at day 120, before definitive crown restoration. The normal PDL space should be noted.

EXAMPLE 6

Patient 6 was a 59 year old male. His tooth #18 had a complete alveolar bone resorption following furcal invasion as shown in FIG. 20(1). This tooth had to be replaced. Tooth #1 (FIG. 20(2)) had been chosen for the transplantation.

The protocol followed during the transplantation was generally the same as the protocol used in Example 1.

Double PDL stimulation protocol was again performed for transplantation. Since the alveolus was too large, the extraction of tooth #18 was performed 21 days before transplantation and the alveolus was carefully curetted to reduce infections sequelae.

FIG. 20(3) shows the suturing technique of the transplanted tooth. An additional bucco-lingual stitch was required to adjust the gingival edge level.

FIG. 20(4) shows a radiography at day 21. The canal was filled with $Ca(OH)_2$. FIG. 20(5) shows complete bone repair at day 180. Two titanium implants were used to replace teeth #19 and #20. FIG. 20(6) shows the clinical condition at day 180. The periodontal state was excellent.

This example illustrates how transplantation and osseointegrated implants are complementary techniques with regard to the state of the bone. Thus, transplantation can be performed even if the receiver site has a large bone defect, while still promoting bone regeneration.

EXAMPLE 7

Patient 7 was an 81 year old male. Teeth #3 and #5, which were bridge abutments showed deep periodontal lesions and had to be extracted (FIG. 21(1)). Tooth #32 (FIG. 21(2)) was used for transplantation into the site of the upper right premolars.

The protocol followed during the transplantation was generally the same as the protocol used in Example 1.

FIG. 21(3+4) show a buccal and a lingual view at month 15. A vertical groove was performed on the buccal coronal side to look like two premolars. FIG. 21(5) shows a radiography at day 120. FIG. 21(6) shows a radiography at month 14. Bone regeneration was clearly seen.

This example illustrates the healing capacity of stimulated PDL in a very old patient.

EXAMPLE 8

Patient 8 was a 52 year old female. Her tooth #13 had a very large periodontal and apical lesion (FIG. 22(1)). Tooth #17, also a bridge abutment, had a deep periodontal pocket. The residual bone between the lesion and the sinus was less than a millimeter thick (FIG. 22(2)).

The protocol followed during the transplantation was generally the same as the protocol used in Example 1.

FIG. 22(3) illustrates the clinical condition after the extraction of teeth #13 and #17 and a curettage.

Tooth #18 (FIG. 22(4)) had very long roots and was used for the transplantation.

Endodontic treatment, hemisection and mobilization were performed (FIG. 22(5)). During the same appointment, the alveolus was prepared on the site of tooth #14; after flap reflexion, the thin bone was carefully opened with a bur and the Schneiderian membrane was carefully removed from the bone surface in the sinus only a few millimeters with special sinus elevators. Then the flap was stitched as illustrated in FIG. 22(6).

15 days later, the two parts of tooth #18 were transplanted on the sites of teeth #13 and #14. The flap was reopened and the Schneiderian membrane was pushed deeper to place the transplanted root in the site of tooth #14 without sinus membrane perforation. In the site of tooth #13, the transplanted root was in the middle of a large area of healing granulation tissue.

The two transplanted half teeth were sutured but their mobility's were very great (FIG. 23(1)). In this situation it was advisable that the patient refrain from mastication on the left side for two months.

At day 15, attachment of the two transplanted half teeth was beginning as shown in FIG. 23(2). Thus, the sutures were removed.

At day 30 (FIG. 23(3)), migration of the tooth in site #13 was occurring. Composite coronal restoration was performed to promote stability between the two parts of the transplanted tooth (FIG. 23(4+5)).

At month 14, mobility of transplanted tooth was normal. FIG. 24 shows the follow-up with a radiographic comparison:

FIG. 24(1): before extraction of teeth #13 and #15. Note the bone resorption around tooth #13 and the thickness of the bone in the site of tooth #14.

FIG. 24(2): day 30.

FIG. 24(3): day 72: bone regeneration around the roots was visible.

FIG. 24(4): month 7: bone density was normal. The teeth were functional.

FIG. 24(5): month 14: the bone density was at a very good level. Cortical and periodontal spaces were clearly identified.

The bone level was identical with its level on the roots before transplantations shown in FIG. 24(6).

This example shows the capacity of stimulated PDL to regenerate bone even if it was completely destroyed.

A continuing study covering 140 transplanted teeth has shown zero ankylosis and resorption phenomenon when using the method of the present invention. The method of transplantation described in the present invention can be used every time there is a non-functional tooth or a root and can be adapted to the replacement of a functional tooth. Furthermore, with osteo-integrated implants, transplantation has no harmful effect on side teeth.

The method of the present invention gives a fully functional result after two to eight weeks and is particularly well adapted for the replacement of teeth suffering from deep periodontal lesion, severe furcation invasions and root fracture, even when the bone alveolus has been strongly damaged.

The present invention also provides a method to regenerate a severely damaged bone because the stimulated desmodont has the potential to regenerate the alveolus bone around the transplanted tooth as well. Moreover, there is no attachment loss compared to the attachment of the tooth in its origin site.

This technique enables the reimplantation of retained teeth, including adults with an atrophied desmodont. This study showed excellent global results; i.e., at about a 97% success rate.

Finally it is possible to state that the tooth-alveolus ligament transmits occlusal strains in a lot more physiological manner than osteo-integration implants.

REFERENCES

Andreasen J O, et al. "Replantation of 400 avulsed permanent incisors. 4. Factors related to periodontal ligament healing." *Endod Dent Traumatol.* 1995 Apr;11(2):76–89.

Andreasen J O, et al., "A long-term study of 370 autotransplanted premolars. Part I. Surgical procedures and standardized techniques for monitoring healing." *Eur J Orthod.* 1990 Feb;12(1):3–13.

Andreasen J. O. "A time related study of periodontal healing and root resorption activity after replantation of mature permanent incisor in monkeys." *Swed Dent J.* 1980; 4:135–144.

Andreasen J. O. "The effect of pulp extirpation of root canal treatment on periodontal healing after replantation of permanent incisors in monkey." *Swed Dent J.* 1981; 7:245–252 and 1982; 8:135–144.

Andreasen J. O. "The effect of splinting upon periodontal healing after replantation of mature permanent incisor in monkeys." *Acta Odontol Scand.* 1975; 33:313–323.

Andreasen J. O. "The effect of excessive splinting upon periodontal and pulpal healing after auto-transplantation of mature and immature permanent incisors in monkey." *Int J; Oral Surg* 1983; 12:239–249.

Andreasen J .O. *Atlas de réimplantation et de transplantation dentaires,* Editors Masson, 1992)

Andreasen J O, et al. "A long-term study of 370 autotransplanted premolars. Part III. Periodontal healing subsequent to transplantation." *Eur J Orthod.* 1990 Feb;12(1):25–37.

Berude J. A., Laurar H., Sanber J. J., Li S. H. "Resorption after physiological and rigid splinting of replanted permanent incisors in monkeys." *J. Endod* 1988; 14:592–600.

Bromlöf, Lindstong, Hedström, Hammarström., "Vitality of periodontal ligament cells after storage of monkey teeth in milk or saliva." *Scand J. Dent Ros.* 1980; 8:441–445.

Gupta S, et al. "Suture splint: an alternative for luxation injuries of teeth in pediatric patients—a case report." *J Clin Pediatr Dent.* 1997 Fall;22(1):19–21.

Hammarström L., Blomlöf L., Feiglin B., Andersson L., Lindskog S. "Replantation of teeth and antibiotic treatment" *Endod Dent Traumatol* 1986; 2:51–59.

Mandel U, et al. "Effect of splinting on the mechanical and histological properties of the healing periodontal ligament in the vervet monkey (Cercopithecus aethiops)." *Arch Oral Biol.* 1989;34(3):209–17.

Nethander, Andersson, Hirtsch "Autogenous free tooth transplantation in man by a 2 stage operation technique. A longitudinal intra individual radiography assessment." *Int J. Oral Maxillofac Surg.* 1988; 17:330–336.

Nyman, Tearing, Lindhe, Planten, "Healing following implantation of periodontitis affected roots into gingival connective tissue" *J. Clin Periodontal.* 1980; 7:394–401.

Oikarinen K S, et al. "Influence of conventional forceps extraction and extraction with an extrusion instrument on cementoblast loss and external root resorption of replanted monkey incisors." *J. Periodontal Res.* 1996 Jul;31(5):337–44.

Oikarinen K "Tooth splinting: a review of the literature and consideration of the versatility of a wire-composite splint." *Endod Dent Traumatol.* 1990 Dec;6(6):237–50. Review.

Oswald, Harrington, Van Hassel "Replantation: The role of the socket" *J. Endod* 1980; 6:479–484.

Sae-Lim V, et al. "Local dexamethasone improves periodontal healing of replanted dogs' teeth." *Endod Dent Traumatol.* 1998 Oct;14(5):232–6.

Trope M, et al. "The role of the socket in the periodontal healing of replanted dogs' teeth stored in ViaSpan for extended periods." *Endod Dent Traumatol.* 1997 Aug;13(4):171–5.

Trope M, et al. "The role of the socket in the periodontal healing of replanted dogs' teeth stored in ViaSpan for extended periods." *Endod Dent Traumatol.* 1997 Aug;13(4):171–5.

Trorstad, Andreasen J. O., Hasselgren G., Kristerson L., Riis I. "Changes in dental tissues after root canal filling with calcium hydroxide" *J. Endod* 1981; 8:17–22.

Van Hassel, Oswald, Harrington "The role of periodontal ligament." *Endod Dent Traumatol.* 1980; 6:506–508.

What is claimed is:

1. A method for transplanting a human or an animal tooth said method comprising the steps of:
   (a) extracting said human or animal tooth to be transplanted from the alveolus of origin;
   (b) suturing immediately said extracted human or animal tooth back into said alveolus of origin;
   (c) waiting for a period of time to facilitate stimulation of the periodontal ligament of said human or animal tooth to be transplanted; and
   (d) transplanting said extracted tooth in a new receiving alveolus.

2. The method according to claim 1, wherein said periodontal ligament is stimulated in about 3 to 30 days.

3. The method according to claim 2, wherein said periodontal ligament is stimulated in about 15 days.

4. The method according to claim 1, wherein said human or animal tooth is a retained tooth or an artifical tooth.

5. The method according to claim 1, wherein said transplanted tooth is selected from the group of a molar, an incisor and a canine.

6. The method according to claim 1, further comprising the step of (e) suturing said transplanted tooth in said new receiving alveolus.

7. The method according to claim 6, wherein said suturing is performed with a bucco lingual suture realized from the central occlusal knot.

8. The method according to claim 1, wherein a mesio distal suture is used in step (b).

9. The method according to claim 1, further comprising the step of preparing the receiving alveolus at the same time as step (b).

10. The method according to claim 9, wherein said receiving alveolus is curetted to suppress granulation tissue.

11. The method according to claim 9, wherein said receiving alveolus is enlarged using a surgical bur.

12. The method according to claim 1, wherein said human or animal tooth is extracted using small progressive rotary and rocking movements.

13. A method for stimulating a desmodont of a human or an animal tooth said method comprising the steps of:
   (a) extracting said human or animal tooth from the alveolus of origin;
   (b) suturing immediately said extracted human or animal tooth back into said alveolus of origin; and
   (c) waiting for a period of time such that a very large quantity of fibroblasts are generated around the tooth alveolus ligament during healing.

14. The method according to claim 13, wherein said large quantity of fibroblasts are on the order of three to ten times greater than the amount of fibroblasts present.

15. The method according to claim 13, wherein said human or animal tooth is a retained tooth or an artificial tooth.

16. The method according to claim 13, wherein said tooth is selected from the group of a molar, an incisor and a canine.

17. A method for regenerating bone, said method comprising the steps of:
   (a) extracting said human or animal tooth to be transplanted from the alveolus of origin;
   (b) suturing immediately said extracted human or animal tooth back into said alveolus of origin;
   (c) waiting for a period of time to regenerate a ligament of said extracted human or animal tooth; and
   (d) placing said extracted tooth in a new alveolus for a period of time to regenerate said bone.

18. The method according to claim 17, wherein said human or animal tooth is a retained tooth.

19. The method according to claim,7, wherein said tooth is selected from the group of a molar, an incisor and a canine.

20. The method according to claim 17, further comprising the step of preparing the receiving alveolus at the same time as step (b).

21. The method according to claim 20, wherein said receiving alveolus is curetted to suppress granulation tissue.

22. The method according to claim 17, wherein said receiving alveolus is enlarged using a surgical bur.

23. The method according to claim 17, wherein said bone is an alveolus bone or a collateral bone.

24. The method according to claim 23, wherein said bone is regenerated in any osseus site.

* * * * *